(12) United States Patent
Shrem

(10) Patent No.: US 6,735,779 B1
(45) Date of Patent: May 18, 2004

(54) VISORED HAT CONSTRUCTION

(76) Inventor: Mitsuko Shrem, 1060 Dunaweal La., Calistoga, CA (US) 94515

( * ) Notice: Subject to any disclaimer, the term of this patent is extended or adjusted under 35 U.S.C. 154(b) by 0 days.

(21) Appl. No.: 10/191,046

(22) Filed: May 29, 2002

(51) Int. Cl.$^7$ .................................................. A61F 9/00
(52) U.S. Cl. ..................................... 2/12; 2/10; 2/209.3
(58) Field of Search ........................... 2/10, 12, 15, 425, 2/209.13, 195.1, 209.3

(56) References Cited

U.S. PATENT DOCUMENTS

| | | | |
|---|---|---|---|
| 2,092,805 A | * 9/1937 | Jones | 2/12 |
| 2,769,308 A | 11/1956 | Krasno | |
| 2,874,387 A | * 2/1959 | Bannister et al. | 2/195.1 |
| 3,585,643 A | 6/1971 | Ryan | |
| 3,811,130 A | 5/1974 | Townsend, Jr. | |
| 3,927,421 A | 12/1975 | Simon | |
| 4,096,589 A | 6/1978 | Goldstein | |
| 4,292,689 A | 10/1981 | Townsend, Jr. | |
| 4,476,589 A | 10/1984 | Burgin et al. | |
| 4,793,006 A | * 12/1988 | Dawson | 2/195.1 |
| 4,945,575 A | 8/1990 | Townsend | |
| 5,091,995 A | * 3/1992 | Oates | 2/209 |
| 5,159,720 A | * 11/1992 | Scott, Jr. | 2/171 |
| 5,487,191 A | * 1/1996 | Ridley | 2/195.1 |
| 5,598,230 A | * 1/1997 | Quaresima | 351/44 |
| 5,781,933 A | * 7/1998 | De Giacomi | 2/195.1 |
| D412,774 S | * 8/1999 | Shwartz | D2/876 |
| 6,009,555 A | * 1/2000 | Siprut | 2/12 |

FOREIGN PATENT DOCUMENTS

FR          1087393         2/1955

OTHER PUBLICATIONS

Siegman, "Chapter 19: Stable Two–Mirror Resonators," *Lasers*, University Science Books, pp. 745 and 746, (1986).

* cited by examiner

*Primary Examiner*—Katherine Moran
(74) *Attorney, Agent, or Firm*—William Michael Hynes; Townsend and Townsend and Crew LLP

(57) ABSTRACT

A lightweight visor of semi-rigid plastic mesh material is sized to provide filtered sun ray incidence with minimum wind resistance to and through to the head of the wearer. The visor is crescent-shaped with the outer and larger curvature of the crescent forming the visor brim and the inner and smaller curvature of the crescent forming the head-contacting surface of the visor. The smaller curvature of the crescent is always maintained with a curvature that is greater than the head of the wearer and is provided with a soft liner disposed in the plane of the visor for contact to the head of the wearer. Provision is made for the removably detachable mounting of light-obstructing shades, each shade occupying less than one-third of the total area of the visor.

2 Claims, 2 Drawing Sheets

VISORED HAT CONSTRUCTION

CROSS-REFERENCES TO RELATED APPLICATIONS

NOT APPLICABLE

STATEMENT AS TO RIGHTS TO INVENTIONS MADE UNDER FEDERALLY SPONSORED RESEARCH OR DEVELOPMENT

NOT APPLICABLE

REFERENCE TO A "SEQUENCE LISTING," A TABLE, OR A COMPUTER PROGRAM LISTING APPENDIX SUBMITTED ON A COMPACT DISK.

NOT APPLICABLE

This invention relates to visors. More particularly, a sun visor is disclosed which is particularly useful for actively played games, such as tennis. The visor stores in a flat disposition, fits to the head in a shaped arcuate disposition, and supports detachably removable shading.

BACKGROUND OF THE INVENTION

Visors are well known. The following are exemplary of such constructions:

Krasno, U.S. Pat. No. 2,769,308 entitled Thermal Applicator for Head illustrates a headband-type visor having an integral bill that can be saturated with water for desired cooling.

Ryan, U.S. Pat. No. 3,585,643 entitled Sun Hat illustrates in a visor the combination of a headband and flat sunshade surface, which is capable of being disposed, at various angles with respect to the sun.

Goldstein, U.S. Pat. No. 4,096,589 entitled Adjustable Eye Shade sets forth a headband with a detachable visor element.

Townsend Jr., U.S. Pat. No. 4,292,689 entitled Visored Hat Construction sets forth a visor and integral headband. The visor surface is disposed in a flat or planar disposition with respect to the head of the wearer. This reference establishes criteria for such visors. Such visors should have:

a) Extraordinary light weight;
b) Unobstructed lateral vision;
c) Low wind resistance;
d) Perspiration and stain resistance;
e) Filtered sun rays incidence to the head of the wearer;
f) Hat size adjustability; and,
g) Structural integrity and durability.

Townsend Jr., U.S. Pat. No. 4,945,575 entitled Sun Visor sets forth a visor and integral headband which is maintained in a planar disposition. Unlike Townsend Jr. '689, the planar visor contains an open cell structure, which tapers in thickness to provide varying overhead light cut-off angles that shield the wearer's eyes from the direct rays of the sun. This provides a headband of increased thickness immediate to the head of the wearer.

BRIEF SUMMARY OF THE INVENTION

A lightweight visor of semi-rigid plastic mesh material is sized to provide filtered sun ray incidence with minimum wind resistance to and through to the head of the wearer. The visor is crescent-shaped with the outer and larger curvature of the crescent forming the visor brim and the inner and smaller curvature of the crescent forming the head-contacting surface of the visor. The smaller curvature of the crescent is always maintained with a curvature that is greater than the head of the wearer and is provided with a soft liner disposed in the plane of the visor for contact with the head of the wearer. Provision is made for the removably detachable mounting of light obstructing shades, each shade occupying less than one-third of the total area of the visor. Banding of the visor at the smaller curvature of the crescent to the head occurs with a soft elastic cord, which is preferably of elastic, spiraled construction. The hat construction has high structural integrity and durability. The visor is mounted to the head by drawing the respective ends of the crescent across the back of the head with a soft elastic cord, enabling a single-size visor to accommodate a wide range of head sizes and shapes. The smaller curvature of the crescent is drawn across the forehead and sides of the head into firm retaining contact at the soft liner imparting maximum perspiration and stain resistance to the visor. When the visor is drawn to the head it forms the crescent-shaped semi-rigid plastic mesh material into an arcuate disposition with the concave side shading the eyes of the wearer. The arcuate configuration of the semi-rigid plastic mesh imparts rigidity, gathers the visor to the head of the wearer with its residual wind resistance, and allows substantially unobstructed lateral vision. The detachably removable light-obstructing shades can be used alone or in combination to prevent sun glare or attenuate brightness.

DETAILED DESCRIPTION OF THE INVENTION

Figure 1:
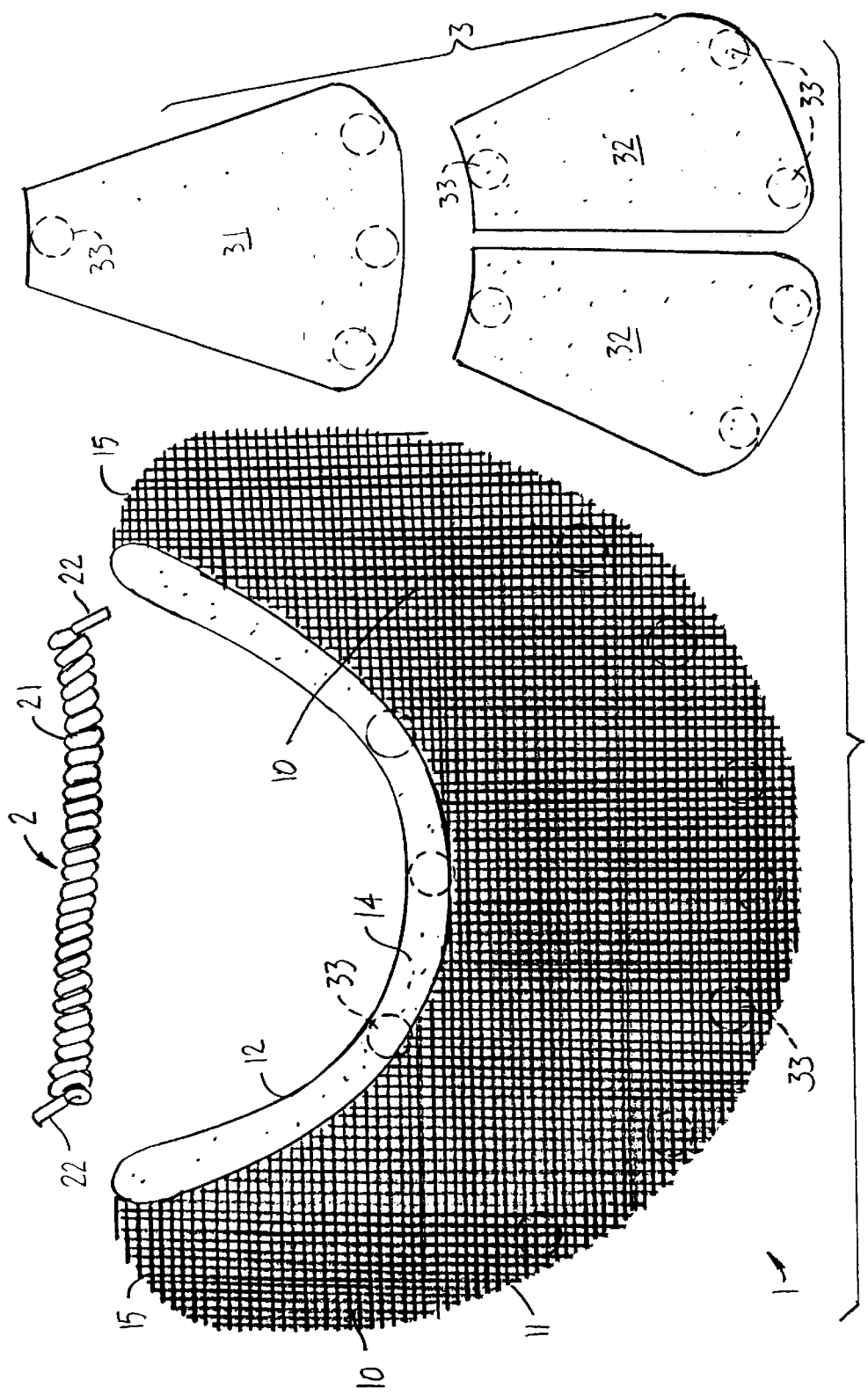
FIG. 1 is a plan view of the crescent-shaped semi-rigid plastic mesh material forming the visor with the soft liner attached at the smaller curvature of the head contacting surface of the visor, with the spiral cord and three detachably removable light-obstructing shades shown separately; and, FIG. 2 is a perspective view of the visor gathered to the head of the wearer by the spiral cord illustrating the installation of a light-obstructing shade to the visor in exploded relation.

Referring to FIG. 1, visor 1 is illustrated with its discrete elements separately displayed. The crescent-shaped semi-rigid plastic mesh material 10 is shown. This material is lightweight, weighing less than one-quarter of a pound. The mesh material is chosen with mesh size to provide filtered sunray incidence through the mesh material. Broadly, mesh sizes in the range between ¼ inch and 1/32 of an inch may be used, most preferably ⅙ of an inch.

Crescent-shaped semi-rigid plastic mesh material 10 should permit reduced wind resistance. First, in sun-exposed active sports such as tennis, such construction permits a cooling flow of air vertically of visor 1, immediate to the forehead of the wearer. Second, during rapid movement or in prevailing winds, there is a reduced tendency of air to scoop the visor from the head of the wearer. Finally, when the visor is gathered to the head of the wearer with an arcuate configuration, residual wind resistance not only prevents scooping of the visor from the head of the wearer but tends to seat the visor as it is forced by the wind to the curvature of the head of the wearer.

Crescent-shaped semi-rigid plastic mesh material 10 is bounded on the brim side of the visor 1 by outer and larger curvature 11. This outer and larger curvature enables the total area of the visor 1 to provide the desired filtered and shaded sun exposure.

Figure 2:
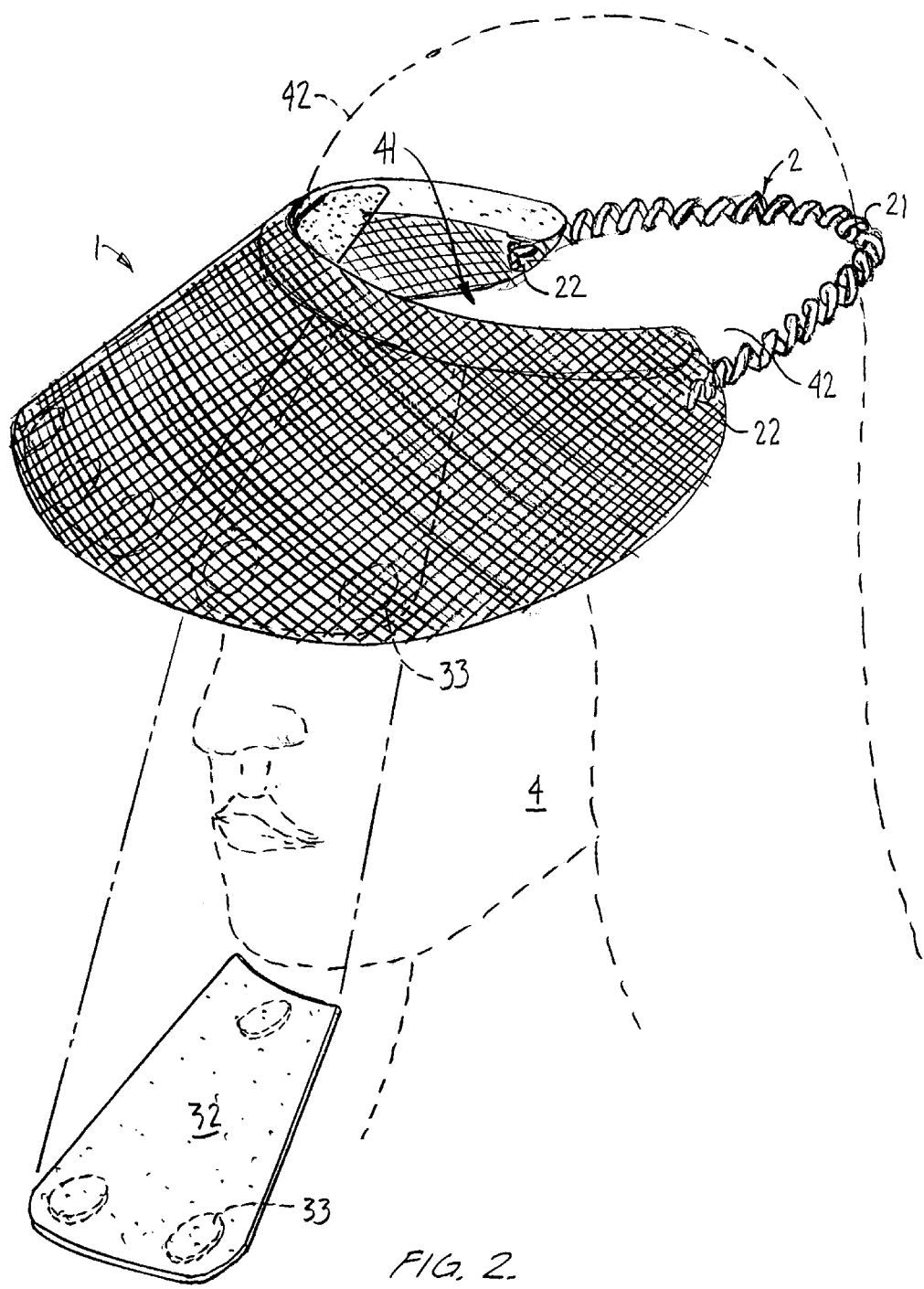

Inner and smaller curvature 12 is provided on the head-contacting side of crescent-shaped semi-rigid plastic mesh material 10. Several important features can be noted. First, and briefly referring to the perspective view of FIG. 2, when plastic mesh material 10 is disposed in the planar disposition, inner and smaller curvature 12 is greater than the natural curvature of wearer 4 at forehead 41 and head sides 42. As will hereinafter be set forth, this curvature allows the visor to form a convex disposition over the eyes of the wearer 41 as the visor is drawn to the head of the wearer. Second, soft liner 14 can be affixed to plastic mesh material 10 to impart both a comfortable fit and perspiration and stain resistance to the visor construction.

Elastic cord 2 fits at the respective crescent ends 15 of plastic mesh material 10. It is preferred that elastic cord 2 is of a spiral construction, preferably fabric covered, and has respective hardened ends 22. Hardened ends 22 can pierce crescent ends 15 of mesh 10, and when suitably wound through the mesh material, form a firm attachment.

Removable shades 3 include central removable shade 31 and two peripheral removable shades 32. To permit the detachably removable fastening of the removable shades 3, Velcro® (a registered trademark of Velcro USA of Manchester, N.H.) shade attachment tabs 33 with hook and loop fasteners are fastened to both the removable shades 3 and the crescent-shaped semi-rigid plastic mesh material 10 at complementary positions.

Placement of visor 1 to the head of wearer 4 is easy to understand. First, elastic cord 2 is threaded to crescent ends 15 at hardened ends 22. Second, the crescent-shaped semi-rigid plastic mesh material 10 is placed to the forehead 41 and head sides 42 of wearer 4. Elastic cord 2 is drawn about the back to the head of wearer 4.

Remembering that inner and smaller curvature 12 has a curvature which is greater than the curvature of the head of wearer 4 at forehead 41 and head sides 42, gathering of visor 1 at elastic cord 2 will cause normally planner crescent-shaped semi-rigid plastic mesh material 10 to move to an arcuate shaped. Contacting forehead 41 first, and drawing to head sides 42 second, the semi-rigid plastic mesh will normally form a concave configuration over the face of the wearer 4. The disposition shown in FIG. 2 will naturally result.

In many active games (certainly in tennis), sun will be addressed to the eyes of the wearer 4 at a more or less constant angle. The tennis player usually faces his/her tennis opponent at a constant angle relative to the sun, especially when serving. Detachably removable sunshades 3 are made for such conditions. By way of example, and with specific reference to FIG. 2, peripheral sunshade 32 is shown in exploded relation with respect to visor 1. By the simple expedient of attaching the complementary Velcro® (a registered trademark of Velcro USA of Manchester. N.H.) shade attachment tabs 33 with hook and loop fasteners one to another, such removable attachment is easily made. Further, and once such shading is no longer needed (as wherein tennis players change sides during a match), the sunshade 3 may easily be removed.

What is claimed is:

1. A lightweight visor for conforming to a curvature of a forehead and sides of a head of a wearer comprising in combination:

a crescent-shaped semi-rigid plastic mesh material having mesh sized to provide filtered sun ray incidence with minimum resistance to and through to the head of the wearer, the crescent-shaped semi-rigid plastic mesh material having an outer and larger curvature forming the visor brim and an inner and smaller curvature forming the head-contacting surface of the visor;

the inner and smaller curvature of the crescent having a curvature which is greater than the curvature of the forehead and the sides of the head of the wearer;

an elastic cord connected to the respective ends of the crescent for drawing the smaller curvature of the crescent to the curvature of the forehead and sides of the head of the wearer whereby the crescent-shaped semi-rigid plastic mesh material is formed into an arcuate disposition with the concave side shading the eyes of the wearer;

at least one removably detachable light-obstructing shade has an area of less than one-third of the crescent-shaped semi-rigid plastic mesh material for selective placement to the visor whereby glare through the visor at a specific angle to the sun is blocked; and, a fastening means on the visor permitting the area of placement of the light-obstructing shade on the visor to be changed relative to eyes of the wearer whereby glare from a specific angle may be blocked by the selective placement of the shade.

2. A lightweight visor for conforming to a curvature of a forehead and sides of a head of a wearer comprising in combination:

a crescent-shaped semi-rigid plastic mesh material having mesh sized to provide filtered sun ray incidence with minimum resistance to and through to the head of the wearer, the crescent-shaped semi-rigid plastic mesh material having an outer and larger curvature forming the visor brim and an inner and smaller curvature forming the head-contacting surface of the visor;

the inner and smaller curvature of the crescent having a curvature which is greater than the curvature of the forehead and the sides of the head of the wearer;

an elastic cord connected to the respective ends of the crescent for drawing the smaller curvature of the crescent to the curvature of the forehead and sides of the head of the wearer whereby the crescent-shaped semi-rigid plastic mesh material is formed into an arcuate disposition with the concave side shading the eves of the wearer; and, a plurality of removably detachable light-obstructing shades having an area of less than one-third of the crescent-shaped semi-rigid plastic mesh material for selective placement to the visor whereby glare through the visor at a specific angle to the sun is blocked.

* * * * *